(12) United States Patent
Fu et al.

(10) Patent No.: US 11,897,923 B2
(45) Date of Patent: Feb. 13, 2024

(54) PANICUM VIRGATUM SOSEKI PROTEIN SOK2, CODING GENE AND APPLICATION THEREOF

(71) Applicant: Qingdao Institute of Bioenergy and Bioprocess Technology, Chinese Academy of Sciences, Shandong (CN)

(72) Inventors: Chunxiang Fu, Qingdao (CN); Yamei Wang, Qingdao (CN); Wenwen Liu, Qingdao (CN); Zhenying Wu, Qingdao (CN); Shiqie Bai, Qingdao (CN); Chuan'en Zhou, Qingdao (CN); Ruijuan Yang, Qingdao (CN); Shanshan Jiang, Qingdao (CN); Mengqi Wang, Qingdao (CN)

(73) Assignee: Qingdao Institute of Bioenergy and Bioprocess Technology, Chinese Academy of Sciences Ltd

( * ) Notice: Subject to any disclaimer, the term of this patent is extended or adjusted under 35 U.S.C. 154(b) by 231 days.

(21) Appl. No.: 17/168,983

(22) Filed: Feb. 5, 2021

(65) Prior Publication Data

US 2022/0153785 A1    May 19, 2022

(51) Int. Cl.
*C07K 14/415* (2006.01)
*C12N 15/82* (2006.01)

(52) U.S. Cl.
CPC ............ *C07K 14/415* (2013.01); *C12N 15/82* (2013.01); *C12N 15/8262* (2013.01)

(58) Field of Classification Search
CPC .............................. C07K 14/415; C12N 15/82
See application file for complete search history.

*Primary Examiner* — Gary B Nickol
*Assistant Examiner* — Amelia Nicole Dickens

(57) ABSTRACT

The present invention relates to a coding gene of the SOSEKI protein SOK2 and an application thereof, wherein through molecular regulation of the SOSEKI protein SOK2, the flowering time of *Panicum virgatum* is delayed, biomass is increased, lignin content in the cell wall of *Panicum virgatum* is reduced and the fermentable sugar yield is boosted.

4 Claims, 3 Drawing Sheets

Specification includes a Sequence Listing.

SEQUENCE LISTING

<160> NUMBER OF SEQ ID NOS: 10

<210> SEQ ID NO 1
<211> LENGTH: 732
<212> TYPE: DNA
<213> ORGANISM: Panicum virgatum

<400> SEQUENCE: 1

```
atggcgctgc cccacagcca caagcagtac gtggacgcct accgggacgc cgccgcagag    60
gatccggagg acgacgagct gggctactcg taccaccacc gccgggccgg cgcgcacgcg   120
gcggggcgc ggctcgcccg gccgacaag cccgccgccg tctcggcccg gaccaaccgg     180
agccgccccg tggagctccc cgtcgaggag acctcgccgc cgtcctcgac ctcctcggac   240
aagccgcccg cgctggcgcc gctgcagccg ggccgggcca agtacccgga gcccgagccg   300
aaccgccccg gctccgtgct cctgcagctg atcgcgtgcg ggtcggggc ggcgggcggc    360
ggctcgggca attgccgcgc cgagccgagg cgcagctgcg ggctggtgag ccggctctcg   420
gcccgcgcgg gcgcggacga ggaggacgac gacgaggacg cggcggcggg gggcgccgac   480
atgggccgcc ggttcgggca cctcgccgtg ccggacaagg agtacttcag cggcagcatc   540
gtggagggcg ccggcggccg cggcacgccg ctgccggcgt cgtcgctcaa gcggtccaac   600
tcgtacaatg aggagaggag gcttggcgtt gggatcggcg aggatggagc ggatgagcag   660
atggaaggcg acggaggagg gatcagggga cggtgcatcc ccggcaggaa gaagcagccg   720
ccgcagaagt ag                                                        732
```

<210> SEQ ID NO 2
<211> LENGTH: 243
<212> TYPE: PRT
<213> ORGANISM: Panicum virgatum

<400> SEQUENCE: 2

```
Met Ala Leu Pro His Ser His Lys Gln Tyr Val Asp Ala Tyr Arg Asp
1               5                   10                  15

Ala Ala Ala Glu Asp Pro Glu Asp Asp Glu Leu Gly Tyr Ser Tyr His
            20                  25                  30

His Arg Arg Ala Gly Ala His Ala Ala Gly Ala Arg Leu Ala Arg Ala
        35                  40                  45

Asp Lys Pro Ala Ala Val Ser Ala Arg Thr Asn Arg Ser Arg Pro Val
    50                  55                  60

Glu Leu Pro Val Glu Glu Thr Ser Pro Ser Ser Thr Ser Ser Asp
65                  70                  75                  80

Lys Pro Pro Ala Leu Ala Pro Leu Gln Pro Gly Arg Ala Glu Tyr Pro
                85                  90                  95

Glu Pro Glu Pro Asn Arg Pro Gly Ser Val Leu Leu Gln Leu Ile Ala
            100                 105                 110

Cys Gly Ser Gly Ala Ala Gly Gly Ser Gly Asn Cys Arg Ala Glu
        115                 120                 125

Pro Arg Arg Ser Cys Gly Leu Val Ser Arg Leu Ser Ala Arg Ala Gly
    130                 135                 140
```

Ala Asp Glu Glu Asp Asp Glu Asp Ala Ala Gly Gly Ala Asp
145                 150                 155                 160

Met Gly Arg Arg Phe Gly His Leu Ala Val Pro Asp Lys Glu Tyr Phe
            165                 170                 175

Ser Gly Ser Ile Val Glu Gly Ala Gly Gly Arg Gly Thr Pro Leu Pro
            180                 185                 190

Ala Ser Ser Leu Lys Arg Ser Asn Ser Tyr Asn Glu Glu Arg Arg Leu
        195                 200                 205

Gly Val Gly Ile Gly Glu Asp Gly Ala Asp Glu Gln Met Glu Gly Asp
    210                 215                 220

Gly Gly Gly Ile Arg Gly Arg Cys Ile Pro Gly Arg Lys Lys Gln Pro
225                 230                 235                 240

Pro Gln Lys

<210> SEQ ID NO 3
<211> LENGTH: 18
<212> TYPE: DNA
<213> ORGANISM: Artificial Sequence
<220> FEATURE:
<223> OTHER INFORMATION: synthetic

<400> SEQUENCE: 3
atggcgctgc cccacagc                                                   18

<210> SEQ ID NO 4
<211> LENGTH: 25
<212> TYPE: DNA
<213> ORGANISM: Artificial Sequence
<220> FEATURE:
<223> OTHER INFORMATION: synthetic

<400> SEQUENCE: 4
tggtgatctg gtctgctact tctgc                                           25

<210> SEQ ID NO 5
<211> LENGTH: 36
<212> TYPE: DNA
<213> ORGANISM: Artificial Sequence
<220> FEATURE:
<223> OTHER INFORMATION: synthetic

<400> SEQUENCE: 5
aaagcaggct ttgactttat ggcgctgccc cacagc                               36

<210> SEQ ID NO 6
<211> LENGTH: 42
<212> TYPE: DNA
<213> ORGANISM: Artificial Sequence
<220> FEATURE:
<223> OTHER INFORMATION: synthetic

<400> SEQUENCE: 6
gctgggtcta gagactttgg tgatctggtc tgctacttct gc                        42

<210> SEQ ID NO 7
<211> LENGTH: 18
<212> TYPE: DNA
<213> ORGANISM: Artificial Sequence
<220> FEATURE:
<223> OTHER INFORMATION: synthetic

<400> SEQUENCE: 7
ttcgtggtgg ccagtaag                                                   18

```
<210> SEQ ID NO 8
<211> LENGTH: 24
<212> TYPE: DNA
<213> ORGANISM: Artificial Sequence
<220> FEATURE:
<223> OTHER INFORMATION: synthetic

<400> SEQUENCE: 8
agagaccaga agacccaggt acag                                              24

<210> SEQ ID NO 9
<211> LENGTH: 21
<212> TYPE: DNA
<213> ORGANISM: Artificial Sequence
<220> FEATURE:
<223> OTHER INFORMATION: synthetic

<400> SEQUENCE: 9
tacttcagcg gcagcatcgt g                                                 21

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
cctcctccgt cgccttccat                                                   20
```

PANICUM VIRGATUM SOSEKI PROTEIN SOK2, CODING GENE AND APPLICATION THEREOF

TECHNICAL FIELD

This invention generally relates to the technical field of plant genetic engineering, and more particularly, to a coding gene of the SOSEKI protein SOK2 relating to plants' unknown functions and an application thereof in increasing the plant biomass and fermentable sugar yield.

BACKGROUND

As the global population explodes, the consumption of fossil energy has soared, which urgently demands development of renewable energies. Biomass energy has become the most promising alternative energy resource for being rich, eco-friendly, clean and renewable. Presently, the research and development of biomass energy are primarily focused on biodiesel and bioethanol, wherein the use of bioethanol has been gradually commercialized. Lignocellulose, a general name for cellulose, hemicellulose and lignin, is the most plentiful and eco-friendly bioethanol raw material in the world. *Panicum virgatum*, which is a tall perennial C4 herbaceous plant, is an important fiber biomass resource used mainly as an energy or forage grass. It grows rapidly, possesses high biomass, is widely adaptable, has strong stress resistance, and is capable of growing on saline-alkali, arid and barren lands. Therefore, increasing the biomass and fermentable sugar yield of *Panicum virgatum* to significantly improve the development and use of its biomass energy is of high practical value. The completion of the entire genome sequencing of *Panicum virgatum*, the creation of gene expression database and the improvement of transformation system effectively ensure the resource for the discovery and identification of functional genes.

SOSEKI (SOK) proteins are proteins which contain DIX-like domains and are extremely conservative in animal and plant evolutions. The functions of SOSEKI (SOK) protein family have not been deeply studied yet. In addition to participating in the cell polar development, studies show that AtSOK2 may also regulate the flowering time of *arabidopsis* after vernalization. AtSOK2 is located 4.7 kb upstream of the same chromosome of the flowering time negative regulation factor FLC, and thus it is also called UPSTREAM OF FLC (UFC: At5g10150). Resembling the FLC, the expression level of the SOK2 is significantly lowered after the vernalization. The expression variations of the FLC and the SOK2 are consistent in different non-vernalized ecotype *arabidopsis* plants. For instance, the transcriptional levels of the FLC and the SOK2 in the late flowering ecotype plants are higher than in early flowering ecotype plants. Moreover, these genes show resembling developmental regulation expression patterns: the transcriptional level descends in germinating seeds, but ascends significantly before the first pair of leaves appear. Similarly, in late flowering *arabidopsis* mutants, the FLC and the SOK2 coordinate to regulate the flowering time according to different gene locus modifications (Finnegan et al, A Cluster of *Arabidopsis* Genes with a Coordinate Response to an Environmental Stimulus. Current Biology, 14: 911-916). Presently, the studies on the function of the SOK gene and its protein in other plants are scanty.

SUMMARY

The purpose of the present invention is to provide a coding gene of the plant SOSEKI protein SOK2 and an application thereof in increasing the plant biomass and fermentable sugar yield. According to the present invention, the technical problems relating to the low biomass energy of plants, insufficient resource of modified genes, as well as the failure of simultaneously meeting the needs of increasing the plant yield and improving the cell wall molecular quality are effectively solved.

To achieve the above purposes, the present invention adopts the following technical solution:

The first purpose of the present is to provide a coding gene of the *Panicum virgatum* SOSEKI protein SOK2, wherein its amino acid sequence is shown in SEQ ID No.2.

The present invention also provides a coding gene of the *Panicum virgatum* SOSEKI protein SOK2, wherein its nucleotide sequence is shown in SEQ ID No.1.

The second purpose of the present invention is to provide a recombinant vector pANIC6B-PvSOK2 containing the gene of the *Panicum virgatum* SOSEKI protein SOK2.

The third purpose of the present invention is to provide a method for improving the expression level of the SOSEKI protein SOK2 in plants, which utilizes the overexpression vector in the second purpose to improve the expression level of the SOK2 in *Panicum virgatum*.

The fourth purpose of the present invention is to provide an application of the *Panicum virgatum* SOSEKI protein SOK2 in regulating the flowering time of plants.

The fifth purpose of the present invention is to provide an application of the *Panicum virgatum* SOSEKI protein SOK2 in increasing the plant biomass and fermentable sugar yield.

To obtain the gene sequence of the SOSEKI protein SOK2 in the CDS region, primers PvSOK2-F and PvSOK2-R are designed on both sides of the PvSOK2 full-length gene sequence according to the *Panicum virgatum* genome information published on the Phytozome website. A 732 bp full-length gene sequence of the SOSEKI protein PvSOK2 is obtained by means of PCR (Polymerase Chain Reaction) amplification. Subsequently, the full-length sequence fragment is recombined and integrated into the overexpression vector pANIC6B based on the Gateway technology. Through adopting the genetic transformation method mediated by the *agrobacterium* EHA105, the gene is transformed into the embryogenic calli of *Panicum virgatum*, thereby obtaining resistant regenerated plants through the hygromycin resistance screening. Finally, the positive transgenic plants are identified by PCR analysis. The test results show that the overexpressing SOK2 effectively delays the flowering time, increases the plant biomass and boosts the fermentable sugar yield.

The core features and the inventive concept of the present invention are the following:

1) The flowering time is an important factor affecting the plant biomass. One of the major research orientations is to delay the flowering time and improve the biomass by means of plant genetic engineering. The present invention adopts the genetic engineering means and the overexpression technology to improve the expression level of the SOSEKI protein SOK2 in *Panicum virgatum*, which ultimately delays the flowering time of *Panicum virgatum* such that the transgenic plants with increased biomass and fermentable sugar yield are obtained. The genetic breeding, as well as the directed molecular design of *Panicum virgatum* and other gramineous plants are of great significance.

2) The present invention focuses on regulating the gene of the *Panicum virgatum* biomass and the cell wall molecular quality. Through adopting advanced genetic engineering technology, the plant biomass and fermentable sugar content are simultaneously regulated, providing a target for the genetic improvement and molecular breeding of perennial forage grasses and other monocotyledon crops.

Compared with the prior art, the present invention has the following advantages:

1) The gene of the SOSEKI protein SOK2 obtained in the present invention is crucial for regulating the flowering time and reducing the lignin content of *Panicum virgatum*, which makes great contribution to obtaining ideal energy plant types through molecular oriented design.
2) The overexpression of the *Panicum virgatum* SOK2 (PvSOK2) significantly delays the flowering time, increases the biomass and boosts the fermentable sugar yield of *Panicum virgatum*, which greatly facilitates the genetic improvement of energy plants and gramineous grasses.
3) The genetically improved plants obtained in the present invention may be integrated into conventional breeding projects, thus providing new germplasm resources for the cultivation of energy plants and gramineous forage crops.

DETAILED DESCRIPTION

Detailed embodiments and drawings are combined hereinafter to further elaborate the technical solution of the present invention.

The materials, reagents and molecular marker probes adopted in the following embodiments may be purchased from the market unless stated otherwise.

Embodiment 1: Cloning of the PvSOK2 Gene

According to the published genome information of *Panicum virgatum* in the Phytozome website, primers PvSOK2-F and PvSOK2-R are designed on both sides of the PvSOK2 full-length sequence. Taking the *Panicum virgatum* cDNA as a template, the PCR amplification is performed with the aforesaid primers.

The primers' sequences are as follows:

```
PvSOK2-F:
                                    (SEQ ID No. 3)
ATGGCGCTGCCCCACAGC

PvSOK2-R:
                                    (SEQ ID No. 4)
TGGTGATCTGGTCTGCTACTTCTGC
```

Figure 1:
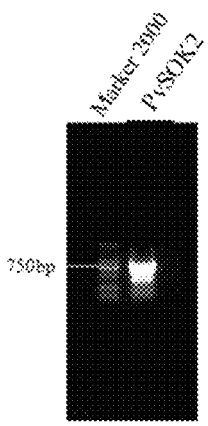
FIG. 1 is an electrophoretogram illustrating the PCR amplification of the plant SOSEKI protein PvSOK2 in *Panicum virgatum*.

The PCR reaction system is: 2 μL of cDNA, 25 μL of 2×Buffer, 4 μL of 10 pM dNTP, 2 μL of 10 μM forward/reverse primer (respectively), 0.5 μL of 5 U/μL PrimerSTAR HS DNA polymerase and 14.5 μL of ddH2O. The sample is added on the ice and then mixed uniformly. The PCR reaction conditions are: 98° C. for 3 minutes; 98° C. for 5 seconds, 56° C. for 15 seconds; 72° C. for 30 seconds, 35 cycles, and 72° C. for 5 minutes. The PCR amplified product is detected by using 1% agarose gel electrophoresis, and then the fragment having a size of about 750 bp are obtained (shown in FIG. 1). The amplified fragment is extracted by using a Promega gel extraction kit and is routinely sequenced by Beijing Genomics Institute. The sequencing results show that the amplified sequence contains a complete open reading frame with a total length of 732 bases. As shown in SEQ ID NO.2, the coding protein contains 243 amino acid residues and the nucleotide sequence is shown in SEQ ID No.1.

Embodiment 2: Construction of Recombinant Vector and Observation of Subcellular Localization by Transient Expression in Tobacco Cells Taking the aforesaid sequence fragment as a template, the PvSOK2 is designed with a primer capable of being seamlessly joined with the expression vector pCABIA1300-cGFP, and the fragment is amplified by using a high-fidelity enzyme. The expression vector is digested by the HindIII restriction enzyme. After the PvSOK2 gene fragment and the pCABIA1300-cGFP vector fragment are extracted, a joining enzyme (purchased from Vazyme company) is adopted to join the two fragments through homologous recombination. The joined product is transformed into *Escherichia coli* DH5a competent cells by heat shock. Monoclonal bacterial colonies are selected and cultured in the liquid LB medium containing kanamycin for PCR amplification and sequencing identification, thereby obtaining the recombinant plasmid pCABIA1300-PvSOK2-cGFP.

The constructed recombinant vector pCABIA1300-PvSOK2-cGFP is transformed into the *agrobacterium* EHA105 and the strain is preserved. The bacterial solution is injected into tobacco by means of the transient expression technology to observe the subcellular localization. The fluorescence confocal results show that, different from typical transcription factors, the PvSOK2 can be localized in not only the tobacco cell nucleus but also the cell membrane, meaning that the gene may have other important biological functions other than functioning as a transcription factor.

Embodiment 3: Obtaining Transgenic *Panicum Virgatum* Plants Using the Overexpressing PvSOK2

The primers PvSOK2-pGWC-F and PvSOK2-pGWC-R for joining an entry vector are designed in the overexpression vector. 18 bases (seamless joining sequence) after the AhdI restriction site and the entry vector pGWC restriction site are introduced at the end of the primers. Taking the obtained PvSOK2 full-length sequence as a template, the PCR amplification is performed with the aforesaid primers.

The primers' sequences are as follows:

```
PvSOK2-pGWC-F:
                                        (SEQ ID No. 5)
AAAGCAGGCTTTGACTTTATGGCGCTGCCCCACAGC

PvSOK2-pGWC-R:
                                        (SEQ ID No. 6)
GCTGGGTCTAGAGACTTTGGTGATCTGGTCTGCT

ACTTCTGC,
``` wherein the underlined portions are the seamless joining sequences.

Figure 2:
FIG. 2 is a conceptual diagram illustrating the overexpression vector of the *Panicum virgatum* pANIC6B-PvSOK2.

The amplified fragments are extracted. The pGWC vector is digested with the AhdI restriction enzyme and is then extracted. A joining enzyme (purchased from Vazyme company) is adopted to join the two fragments through homologous recombination. The joined product is transformed into *Escherichia coli* DH5a competent cells by heat shock. Monoclonal colonies are selected and cultured in the liquid LB medium containing kanamycin for sequencing identification. The recombinant strain plasmid is extracted and sequenced correctly by using the reagent kit, and the recombinant plasmid extracted fragments are integrated into the overexpression vector pANIC6B using the Gateway technology (shown in FIG. 2). The recombinant reaction is as follows: 100 ng of extracted fragments, 50 ng of pANIC6B vector plasmid, 1 µL of LR enzyme (Invitrogen, product No.: 11791020), supplementing to 10 µL with ddH$_2$O; subsequently, culturing at a temperature of 25° C. for 6 hours, transforming into *Escherichia coli* DH5 competent cells to obtain the positive recombinant strain plasmid pANIC6B-PvSOK2 with correct sequencing, and then transforming into the *agrobacterium* EHA105.

Figure 3:
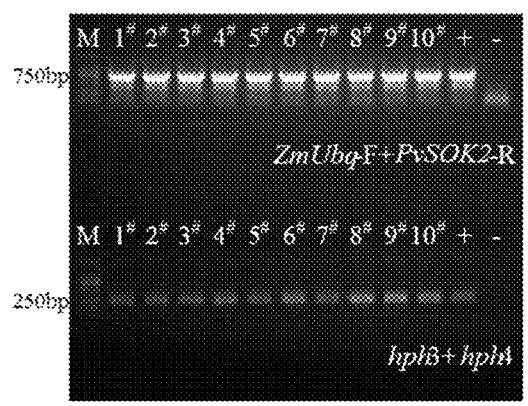
FIG. 3 is a conceptual diagram illustrating the PCR result of the PvSOK2 overexpression transgenic *Panicum virgatum* plants, wherein 1 #-10 #represent the PvSOK2 overexpression transgenic *Panicum virgatum* plants, + represents the pANIC6B-PvSOK2 plasmid; – represents the wild *Panicum virgatum* plant and M represents the DL2000 DNA maker.

In the method (Xi et al, *Agrobacterium-mediated transformation of switchgrass and inheritance of the transgenes.* 2009, *Bioenergy Research*, 2: 275-283), the pANIC6B-PvSOK2 is introduced into the lowland wild *Panicum virgatum* Alamo to obtain resistant seedlings, the vector universal primer ZmUbq-F and the downstream primer PvSOK2-R of the target gene are used to detect the target gene, and upstream and downstream primers (hph3+hph4) of the hygromycin-resistant gene are used to detect the hygromycin gene, thus finally determining the positive transgenic lines (shown in FIG. 3).

Embodiment 4: Molecular Identification of Transgenic Plants

The tender stem tissues of the aforesaid identified transgenic plants are taken and the total RNA is extracted by using a TriZol® (guanidinium thiocyanate) reagent kit (Invitrogen, product No.: 15596026). The content and purity of the total RNA are detected by using an agarose gel electrophoresis and nucleic acid analyzer (NanoDrop® (microvolume spectrophotometer)). Subsequently, 1.0 µg of total RNA is taken for reverse transcription, and a reverse transcriptase (Promega, product No.: M1701) is adopted to reverse-transcriptase it into cDNA, wherein the reverse transcriptional reaction process is referred to the Instructions. Taking the aforesaid cDNA as a template, the primers PvSOK2-qRT-F and PvSOK2-qRT-R are used for fluorescent quantitative PCR detection, and the reference gene is the Ubiquitin (UBQ) gene of *Panicum virgatum*. The sequences of the primers are as follows:

```
PvUBQ-F:
                                        (SEQ ID No. 7)
TTCGTGGTGGCCAGTAAG

PvUBQ-R:
                                        (SEQ ID No. 8)
AGAGACCAGAAGACCCAGGTACAG

PvSOK2-qRT-F:
                                        (SEQ ID No. 9)
TACTTCAGCGGCAGCATCGTG

PvSOK2-qRT-R:
                                        (SEQ ID No. 10)
CCTCCTCCGTCGCCTTCCAT
```

Figure 4:
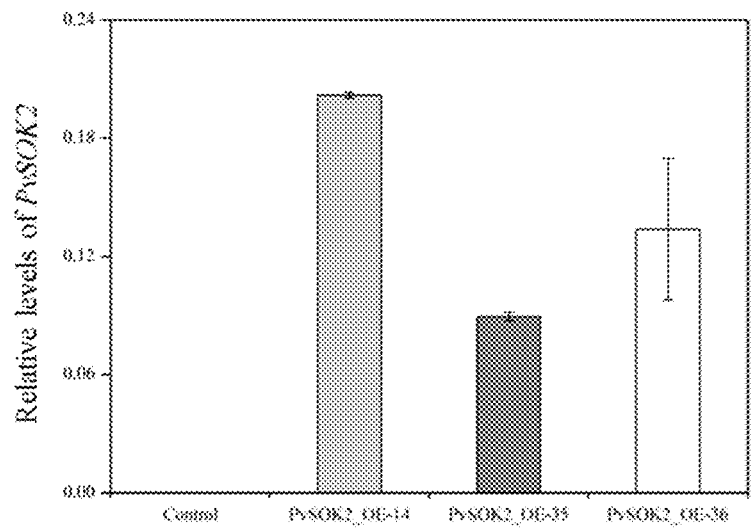
FIG. 4 is a conceptual diagram illustrating the qRT-PCR result of the PvSOK2 gene in the PvSOK2 overexpression transgenic *Panicum virgatum* plants, wherein Control represents the wild *Panicum virgatum* plant, and PvSOK2_OE-14/-35/-36 respectively represent three independent positive transgenic lines.

The real-time fluorescent quantitative PCR reaction system is 20 µL, including 1 µL of forward/reverse primer (respectively), 2 µL of cDNA template, 10 µL of SYBR Green qRT Master Mix (purchased from Takara Bio Inc.) and ddH2O (supplements to 20 µL). The model no. of the real-time fluorescent quantitative PCR is Roche480 and a two-step method is adopted to perform the reaction. The test results show that, compared with the wild Control, the expression levels of the PvSOK2 in the transgenic plants PvSOK2_OE-14, PvSOK2_OE-35 and PvSOK2_OE-36 are significantly increased (shown in FIG. 4).

Figure 5:
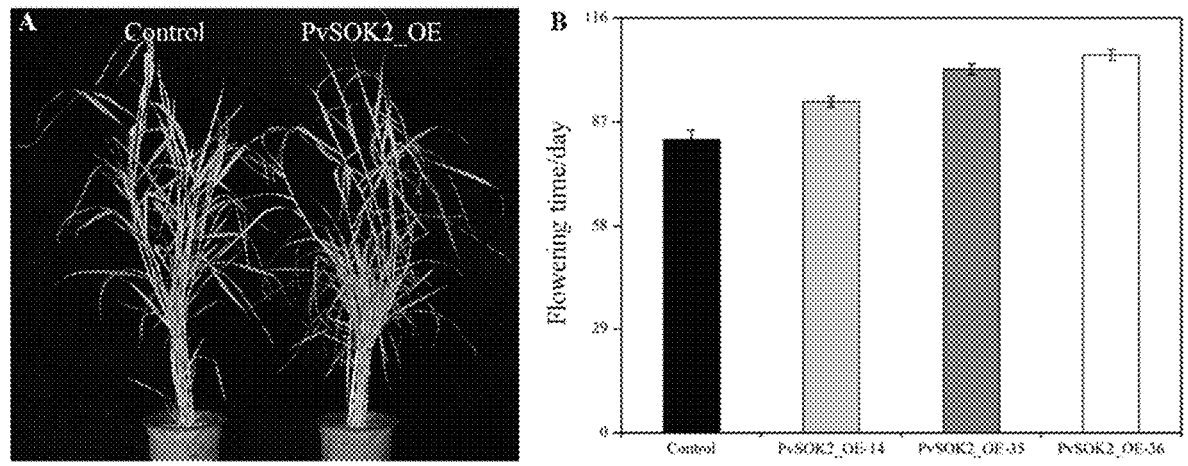
FIG. 5 is a conceptual diagram illustrating the statistical result of phenotype (A) and flowering time (B) of the PvSOK2OE transgenic and wild *Panicum virgatum* plants, wherein Control represents the wild *Panicum virgatum* plant, and PvSOK2_OE-14/-35/-36 respectively represent three independent positive transgenic lines.
Figure 6:
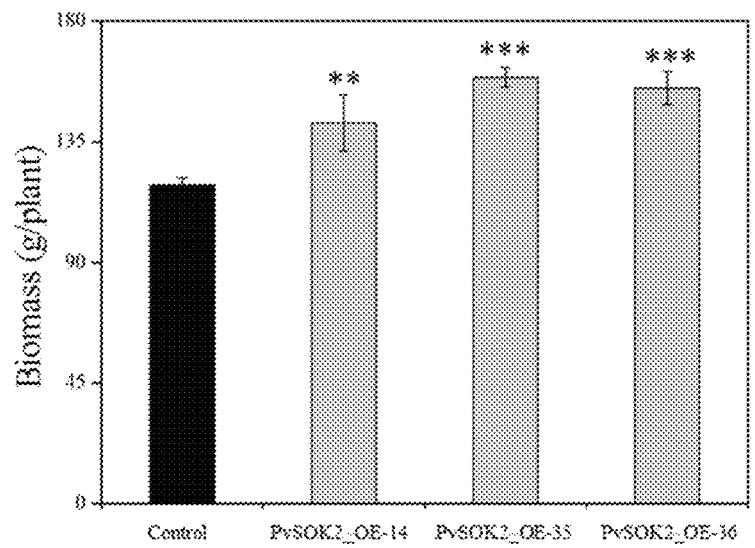
FIG. 6 is a conceptual diagram illustrating the test result of the biomass of the PvSOK2OE transgenic and wild *Panicum virgatum* plants, wherein Control represents the wild *Panicum virgatum* plant, and PvSOK2_OE-14/-35/-36 respectively represent three independent positive transgenic lines.
Figure 7:
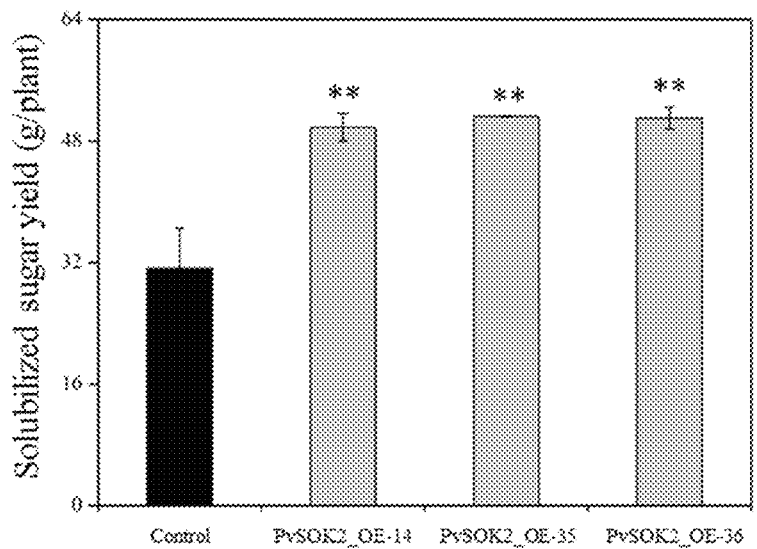
FIG. 7 is a conceptual diagram illustrating the test result of fermentable sugar yield of the PvSOK2OE transgenic and wild *Panicum virgatum* plants, wherein Control represents the wild *Panicum virgatum* plant, and PvSOK2_OE-14/-35/-36 respectively represent three independent positive transgenic lines.

Embodiment 5: Analysis of Flowering Time, Biomass and Fermentable Sugar Yield of Transgenic Plants The flowering time and biomass of the transgenic plants growing for 6 months are measured. Compared with the control plant, the flowering time of transgenic plants is delayed (shown in FIG. 5). The aboveground materials of the Control and the PvSOK2¬_OE-14/-35/-36 plants growing for 6 months are collected and their fresh weights are measured respectively. The results show that the biomass of transgenic plants is increased by 19.3-33.6% compared with that of the wild plant (shown in FIG. 6). The fermentable sugar yield is detected by using the phenol sulfate method, wherein the specific detecting process is: using the cellulase and cellobiase mixture for the direct enzymatic hydrolysis of cell wall residues for 72 hours, and then taking it as the Control; using 1.5% H$_2$SO$_4$ to pretreat at a temperature of 121° C. for 60 minutes, and using the same amount of cellulase and cellobiase mixture for the enzymatic hydrolysis of cell wall residues for 72 hours, and then taking it as the treatment group. The fermentable sugar content in the enzymatic hydrolysis product is detected by using the phenol sulfate method (Dubois et al, *Colorimetric Method for Determination of Sugars and Related Substances.* 1956, *Analytical Chemistry*, 28: 350-356). The saccharification efficiency is the ratio between the difference of fermentable sugar content before and after the enzymatic hydrolysis and the fermentable sugar content before the enzymatic hydrolysis. Thus, according to the following formula: fermentable sugar yield (g/plant)=carbohydrate yield (g/plant) in above-ground cell wall×saccharification efficiency, the fermentable sugar yield of transgenic plants calculated out is increased by about 65% compared with the wild plant (shown in FIG. 7).

The general principle defined in the specification may be realized in other embodiments without departing from the spirit or scope of the present invention. Therefore, the present invention is not limited to the aforesaid embodiments but to the widest scope consistent with the principles and inventive features disclosed in the present invention.

What is claimed is:

1. A cDNA encoding for a *Panicum virgatum* SOSEKI protein, said cDNA comprising SEQ ID No. 1.

2. The cDNA of claim 1, wherein the SOSEKI protein comprises the amino acid sequence of SEQ ID No. 2.

3. The cDNA of claim 1, wherein the nucleotide sequence is contained within the expression vector pANIC6B-PvSOK2.

4. An expression vector to express the *Panicum virgatum* SOSEKI protein, wherein the expression vector is pANIC6B-PvSOK2, and wherein the PvSOK2 sequence is the nucleotide sequence SEQ ID NO. 1.

* * * * *